(12) United States Patent
Watanabe

(10) Patent No.: US 10,105,517 B2
(45) Date of Patent: Oct. 23, 2018

(54) CATHETER WITH ADJUSTABLE GUIDEWIRE EXIT POSITION

(71) Applicant: TELEFLEX MEDICAL INCORPORATED, Research Triangle Park, NC (US)

(72) Inventor: Gwen Watanabe, Wayne, PA (US)

(73) Assignee: TELEFLEX MEDICAL INCORPORATED, Research Triangle Park, NC (US)

( * ) Notice: Subject to any disclaimer, the term of this patent is extended or adjusted under 35 U.S.C. 154(b) by 463 days.

(21) Appl. No.: 14/827,357

(22) Filed: Aug. 17, 2015

(65) Prior Publication Data

US 2015/0352329 A1 Dec. 10, 2015

Related U.S. Application Data

(62) Division of application No. 13/871,662, filed on Apr. 26, 2013, now Pat. No. 9,126,013.

(60) Provisional application No. 61/639,527, filed on Apr. 27, 2012.

(51) Int. Cl.
*A61M 25/01* (2006.01)
*A61M 25/00* (2006.01)

(52) U.S. Cl.
CPC .... *A61M 25/0169* (2013.01); *A61M 25/0026* (2013.01); *A61M 25/01* (2013.01); *A61M 25/0043* (2013.01); *A61M 25/0172* (2013.01); *A61M 2025/0035* (2013.01); *A61M 2025/0037* (2013.01); *A61M 2025/0183* (2013.01); *A61M 2025/0188* (2013.01)

(58) Field of Classification Search
CPC .......... A61M 25/0026; A61M 25/0028; A61M 25/0029; A61M 25/01; A61M 25/0102; A61M 25/0169; A61M 2025/0035; A61M 2025/0037; A61M 2025/0063; A61M 2025/018; A61M 2025/0183; A61M 2025/0186; A61M 2025/0188
See application file for complete search history.

(56) References Cited

U.S. PATENT DOCUMENTS

| | | |
|---|---|---|
| 396,754 A | 1/1899 | Mayfield |
| 4,030,503 A | 6/1977 | Clark, III |
| 4,273,128 A | 6/1981 | Lary |
| 4,646,742 A | 3/1987 | Packard et al. |
| 4,649,922 A | 3/1987 | Wiktor |
| 4,706,671 A | 11/1987 | Weinrib |
| 4,762,130 A | 8/1988 | Fogarty et al. |
| 4,813,934 A | 3/1989 | Engelson et al. |
| 4,848,342 A | 7/1989 | Kaltenbach |
| 4,848,344 A | 7/1989 | Sos et al. |
| 4,890,611 A | 1/1990 | Monfort et al. |
| 4,921,478 A | 5/1990 | Solano et al. |
| 5,011,488 A | 4/1991 | Ginsburg |
| 5,032,113 A | 7/1991 | Burns |

(Continued)

FOREIGN PATENT DOCUMENTS

WO WO2008117256 A2 10/2008
WO WO2008117257 A2 10/2008

*Primary Examiner* — Andrew Gilbert
(74) *Attorney, Agent, or Firm* — Baker & Hostetler LLP

(57) ABSTRACT

Catheters including those having guidewire lumens that can convert from an Over-the-Wire mode to a Rapid Exchange mode are useful and effective when this conversion happens without adjusting the position of the guidewire in a body lumen.

18 Claims, 3 Drawing Sheets

(56) References Cited

U.S. PATENT DOCUMENTS

| | | |
|---|---|---|
| 5,035,705 A | 7/1991 | Burns |
| 5,059,176 A | 10/1991 | Winters |
| 5,085,636 A | 2/1992 | Burns |
| 5,100,388 A | 3/1992 | Behl et al. |
| 5,100,423 A | 3/1992 | Fearnot |
| 5,135,494 A | 8/1992 | Engelson et al. |
| 5,141,518 A | 8/1992 | Hess et al. |
| 5,171,221 A | 12/1992 | Samson |
| 5,176,698 A | 1/1993 | Burns et al. |
| 5,192,286 A | 3/1993 | Phan et al. |
| 5,192,290 A | 3/1993 | Hilal |
| 5,192,295 A | 3/1993 | Danforth et al. |
| 5,195,978 A | 3/1993 | Schiffer |
| 5,207,229 A | 5/1993 | Winters |
| 5,211,651 A | 5/1993 | Reger et al. |
| 5,217,434 A | 6/1993 | Arney |
| 5,221,260 A | 6/1993 | Burns et al. |
| 5,259,839 A | 11/1993 | Burns |
| 5,263,932 A | 11/1993 | Jang |
| 5,295,959 A | 3/1994 | Gurbel et al. |
| 5,303,714 A | 4/1994 | Abele et al. |
| 5,304,198 A | 4/1994 | Samson |
| 5,308,356 A | 5/1994 | Blackshear, Jr. et al. |
| 5,312,340 A | 5/1994 | Keith |
| 5,320,604 A | 6/1994 | Walker et al. |
| 5,338,295 A | 8/1994 | Cornelius et al. |
| 5,342,301 A | 8/1994 | Saab |
| 5,364,354 A | 11/1994 | Walker et al. |
| 5,372,601 A | 12/1994 | Lary |
| 5,378,238 A | 1/1995 | Peters et al. |
| 5,380,282 A | 1/1995 | Burns |
| 5,383,856 A | 1/1995 | Bersin |
| 5,385,152 A | 1/1995 | Abele et al. |
| 5,395,335 A | 3/1995 | Jang |
| 5,416,634 A | 5/1995 | Ning |
| 5,423,846 A | 6/1995 | Fischell |
| 5,437,632 A | 8/1995 | Engelson |
| 5,454,788 A | 10/1995 | Walker et al. |
| 5,454,789 A | 10/1995 | Burns et al. |
| 5,464,395 A | 11/1995 | Faxon et al. |
| 5,476,477 A | 12/1995 | Burns |
| 5,484,408 A | 1/1996 | Burns |
| 5,484,409 A | 1/1996 | Atkinson et al. |
| 5,527,326 A | 6/1996 | Hermann et al. |
| 5,554,118 A | 9/1996 | Jang |
| 5,569,195 A | 10/1996 | Saab |
| 5,569,201 A | 10/1996 | Burns |
| 5,571,122 A | 11/1996 | Kelly et al. |
| 5,624,396 A | 4/1997 | McNamara et al. |
| 5,643,298 A | 7/1997 | Nordgren et al. |
| 5,658,302 A | 8/1997 | Wicherski et al. |
| 5,662,603 A | 9/1997 | Gelbfish |
| 5,665,098 A | 9/1997 | Kelly et al. |
| 5,683,410 A | 11/1997 | Samson |
| 5,693,015 A | 12/1997 | Walker et al. |
| 5,728,067 A | 3/1998 | Enger |
| 5,749,849 A | 5/1998 | Engelson |
| 5,766,191 A | 6/1998 | Trerotola |
| 5,776,099 A | 7/1998 | Tremulis |
| 5,843,103 A | 12/1998 | Wulfman |
| 5,868,768 A | 2/1999 | Wicherski et al. |
| 5,895,398 A | 4/1999 | Wensel et al. |
| 5,906,606 A | 5/1999 | Chee et al. |
| 5,919,162 A | 7/1999 | Burns |
| 5,947,985 A | 9/1999 | Imran |
| 5,954,737 A | 9/1999 | Lee |
| 5,972,019 A | 10/1999 | Engelson et al. |
| 5,980,486 A | 11/1999 | Enger |
| 6,004,328 A | 12/1999 | Solar |
| 6,007,517 A * | 12/1999 | Anderson ............ A61M 25/104 604/103.04 |
| 6,007,522 A | 12/1999 | Agro et al. |
| 6,017,323 A | 1/2000 | Chee |
| 6,036,717 A | 3/2000 | Mers Kelly et al. |
| 6,050,972 A | 4/2000 | Zadno-Azizi et al. |
| 6,066,158 A | 5/2000 | Engelson et al. |
| 6,090,126 A | 7/2000 | Burns |
| 6,096,055 A | 8/2000 | Samson |
| 6,129,708 A | 10/2000 | Enger |
| 6,146,396 A | 11/2000 | Konya et al. |
| 6,231,543 B1 | 5/2001 | Hegde et al. |
| 6,245,040 B1 | 6/2001 | Inderbitzen et al. |
| 6,283,950 B1 | 9/2001 | Appling |
| 6,306,124 B1 | 10/2001 | Jones et al. |
| 6,306,151 B1 | 10/2001 | Lary |
| 6,350,252 B2 | 2/2002 | Ray et al. |
| 6,440,097 B1 | 8/2002 | Kupiecki |
| 6,454,775 B1 | 9/2002 | Demarais et al. |
| 6,511,492 B1 | 1/2003 | Rosenbluth et al. |
| 6,517,273 B2 | 2/2003 | Koyama et al. |
| 6,530,935 B2 | 3/2003 | Wensel et al. |
| 6,542,781 B1 | 4/2003 | Koblish et al. |
| 6,575,933 B1 | 6/2003 | Wittenberger et al. |
| 6,589,206 B1 | 7/2003 | Sharkawy et al. |
| 6,610,077 B1 | 8/2003 | Hancock et al. |
| 6,620,179 B2 | 9/2003 | Boock et al. |
| 6,626,861 B1 | 9/2003 | Hart et al. |
| 6,638,245 B2 | 10/2003 | Miller et al. |
| 6,660,014 B2 | 12/2003 | Demarais et al. |
| 6,666,874 B2 | 12/2003 | Heitzmann et al. |
| 6,679,860 B2 | 1/2004 | Stiger |
| 6,685,722 B1 | 2/2004 | Rosenbluth et al. |
| 6,711,444 B2 | 3/2004 | Koblish |
| 6,746,442 B2 * | 6/2004 | Agro ............... A61M 25/0028 604/523 |
| 6,824,545 B2 | 11/2004 | Sepetka et al. |
| 6,945,977 B2 | 9/2005 | Demarais et al. |
| 7,004,954 B1 | 2/2006 | Voss et al. |
| 7,037,293 B2 * | 5/2006 | Carrillo ............... A61B 1/018 604/103.04 |
| 7,058,456 B2 | 6/2006 | Pierce |
| 7,070,576 B2 | 7/2006 | O'Brien et al. |
| 7,186,237 B2 | 3/2007 | Meyer et al. |
| 7,229,431 B2 * | 6/2007 | Houser ............... A61F 2/95 604/103.04 |
| 7,250,042 B2 | 7/2007 | Kataishi et al. |
| 7,264,001 B2 | 9/2007 | Boutillette et al. |
| 7,306,617 B2 | 12/2007 | Majercak |
| 7,338,501 B2 | 3/2008 | Teague et al. |
| 7,377,931 B2 | 5/2008 | Bagaoisan |
| 7,462,183 B2 | 12/2008 | Behl et al. |
| 7,507,246 B2 | 3/2009 | McGuckin et al. |
| 7,517,352 B2 | 4/2009 | Evans et al. |
| 7,758,604 B2 | 7/2010 | Wu et al. |
| 7,879,066 B2 | 2/2011 | Desai et al. |
| 7,883,516 B2 | 2/2011 | Huang et al. |
| 8,216,294 B2 * | 7/2012 | Johnson ............... A61F 2/856 606/108 |
| 2001/0031979 A1 | 10/2001 | Ricci |
| 2001/0031981 A1 | 10/2001 | Evans et al. |
| 2002/0103472 A1 * | 8/2002 | Kramer ............ A61M 25/0023 604/507 |
| 2002/0133117 A1 | 9/2002 | Zadno-Azizi et al. |
| 2002/0143251 A1 | 10/2002 | Richardson et al. |
| 2002/0177870 A1 | 11/2002 | Sepetka et al. |
| 2003/0004542 A1 | 1/2003 | Wensel et al. |
| 2003/0055377 A1 | 3/2003 | Sirhan et al. |
| 2003/0120208 A1 | 6/2003 | Houser et al. |
| 2004/0097904 A1 * | 5/2004 | Carrillo ............... A61B 1/018 604/528 |
| 2004/0133232 A1 | 7/2004 | Rosenbluth et al. |
| 2004/0143286 A1 * | 7/2004 | Johnson ............... A61F 2/856 606/194 |
| 2004/0243156 A1 | 12/2004 | Wu et al. |
| 2004/0260205 A1 | 12/2004 | Boutillette et al. |
| 2005/0131453 A1 | 6/2005 | Parodi |
| 2006/0074442 A1 | 4/2006 | Noriega et al. |
| 2006/0106407 A1 | 5/2006 | McGuckin et al. |
| 2006/0200047 A1 | 9/2006 | Galdonik et al. |
| 2007/0016244 A1 | 1/2007 | Behl et al. |
| 2007/0038225 A1 | 2/2007 | Osborne |
| 2007/0129752 A1 | 6/2007 | Webler et al. |
| 2007/0239182 A1 | 10/2007 | Glines et al. |
| 2008/0064930 A1 | 3/2008 | Turliuc |

(56) References Cited

U.S. PATENT DOCUMENTS

| | | |
|---|---|---|
| 2008/0125798 A1 | 5/2008 | Osborne et al. |
| 2008/0177277 A1 | 7/2008 | Huang et al. |
| 2008/0200873 A1 | 8/2008 | Espinosa et al. |
| 2008/0228209 A1 | 9/2008 | DeMello et al. |
| 2008/0262487 A1 | 10/2008 | Wensel et al. |
| 2008/0269798 A1 | 10/2008 | Ramzipoor et al. |
| 2008/0306440 A1 | 12/2008 | Hirszowicz et al. |
| 2009/0018549 A1 | 1/2009 | Desai et al. |
| 2009/0018569 A1 | 1/2009 | Desai et al. |
| 2009/0076539 A1 | 3/2009 | Valaie |
| 2011/0004197 A1* | 1/2011 | Sansoucy .......... A61M 25/0102 604/523 |
| 2014/0276635 A1* | 9/2014 | Lafitte ............... A61M 25/0169 604/517 |

* cited by examiner

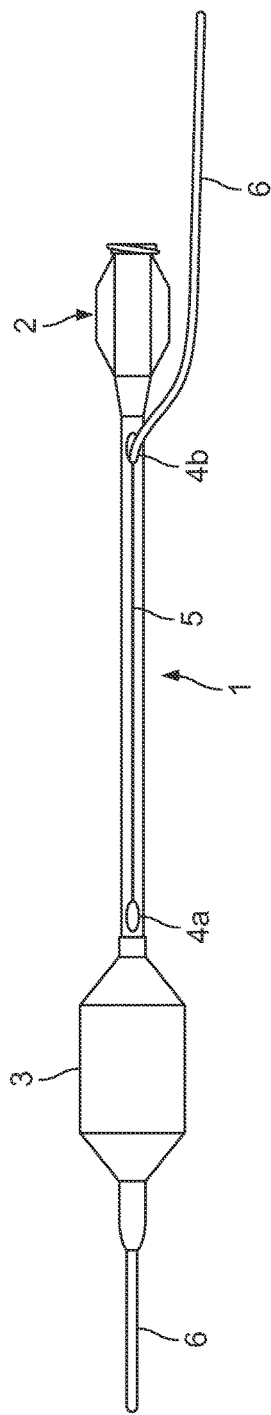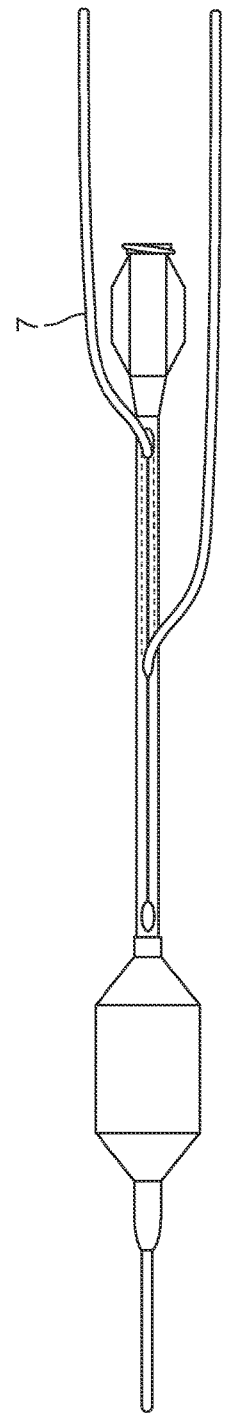
FIG. 2A
FIG. 2B
FIG. 2C

CATHETER WITH ADJUSTABLE GUIDEWIRE EXIT POSITION

RELATED APPLICATIONS

This application is a divisional of U.S. patent application Ser. No. 13/871,662, filed Apr. 26, 2013, now U.S. Pat. No. 9,126,013, which claims the benefit of U.S. Provisional Application Ser. No. 61/639,527, filed Apr. 27, 2012, where the contents of both are hereby incorporated by this reference as set forth herein in their entirety. Likewise, incorporated expressly by reference is U.S. Pat. No. 8,043,313, issued Oct. 25, 2011.

FIELD OF THE DISCLOSURE

The art defines a strong and unrequited need for novel catheter designs, including those having guidewire lumens that can convert from an Over-the-Wire mode to a Rapid Exchange mode.

BACKGROUND OF THE DISCLOSURE

Numerous procedures requires the use of different types of medical devices and the preferred approach is to have systems that can accommodate the need to rapidly convert from one apparatus type to another during procedures.

It is therefore desirable to provide a guidewire for such procedures, which works with a novel catheter system to allow for different functional aspects to be exercised through a common set-up.

BRIEF DESCRIPTION OF THE FIGURES

FIGS. 2A, 2B and 2C likewise each illustrate schematized views of a novel catheter set according to the teachings of the present invention;

SUMMARY OF THE DISCLOSURE

Figure 1:
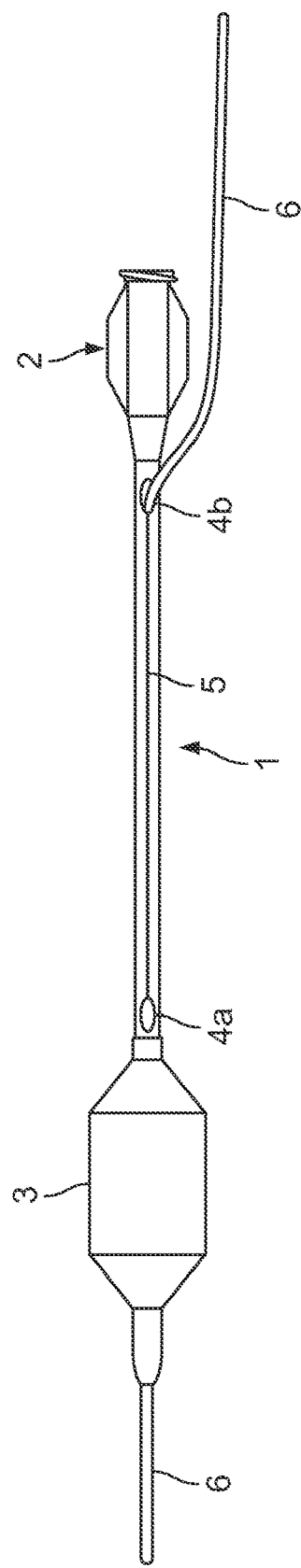
FIG. 1 shows a schematized view of a novel catheter set according to the teachings of the present invention.

According to embodiments, the present disclosure provides a novel catheter design, comprising, in combination; at least a guidewire lumen that can convert from an Over-the-Wire mode to a Rapid Exchange mode, without adjusting the position of the guidewire in a body lumen.

According to embodiments there is provided a method for pushing a guidewire out of a guidewire lumen, comprising, in combination; providing a catheter system having a plurality of lumens, at least a proximate and a distal exit point with a slit disposed therebetween and an ejector wire; pulling the guidewire in a direction transverse to the catheter's longitudinal axis to initiate pulling it pulling out of the slit; inserting the ejector wire into a proximal exit port; advancing the ejector wires down the guidewire lumen; causing the guidewire to pop out of the slit until the ejector wire and the guidewire reach the distal exit point; and withdrawing the ejector wire, leaving the catheter with the guidewire in the distal exit point.

There has thus been outlined, rather broadly, certain embodiments of the guidewire device which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

DETAILED DESCRIPTION

The present inventor has discovered that novel catheter designs, including those having guidewire lumens that can convert from an Over-the-Wire mode to a Rapid Exchange mode are useful and effective when crafted such that this conversion happens without adjusting the position of the guidewire in a body lumen.

Referring now to the Figures, FIG. 1 illustrates that the catheter is comprised of elongate tubular member (1) having distal and proximal ends. Hub or other connecting device (2) is present on the proximal end of the device. Therapeutic element (3), such as a balloon, stent, or other structure, is present on the distal end of the device. Elongate tubular member (1) includes at least a guidewire lumen, and may contain other lumens such as balloon inflation lumens, aspiration lumens, pull/push wire lumens, or any other elongate structures required to operate therapeutic element (3) or other desired functions of the device.

As would be known to artisans, catheter (1) also contains two guidewire exit points (4) along the device. Distal guidewire exit point (4a) is located near the distal end of the device, while proximal guidewire exit point (4b) is located near the proximal end of the device. Slit (5) is made between the two guidewire exit points (4). This Figure shows guidewire (6) existing within the guidewire lumen from the devices distal tip to the proximal guidewire exit point (4b).

FIG. 2 illustrates the mechanism of transitioning a guidewire from its proximal exit point (4b) to its distal exit point (4a). In specific, FIG. 2A shows guidewire (6) is in proximal guidewire exit point (4b). This is a similar condition to a device having an Over-The-Wire construction as the guidewire exits near the proximal end of the catheter.

FIG. 2B shows guidewire (6) being pushed out of guidewire lumen using ejector wire (7). To use the ejector wire, the user first pulls the guidewire (6) in a transverse direction to the catheter long direction to initiate it pulling out of the slit (5). The ejector wire (7) is then inserted into the proximal exit port (4b) and advanced down the guidewire lumen. As the ejector wire progresses, it causes the guidewire to pop out of the slit until the guidewire (6) and ejector wire (7) reach the distal exit point (4a). The ejector wire (7) may then be withdrawn, leaving the catheter with the guidewire in the distal exit point (4a).

FIG. 2C illustrates the ejector wire removed and the guidewire in the distal exit point, the device is in a similar condition as a device having a Rapid-Exchange construction.

Turning now also to FIG. 3, this depiction shows a cross-sectional view of the previously illustrated catheter (1), illustrating how guidewire (6) is pushed from slit (5) in the guidewire lumen when using ejector wire (7).

Figure 3A:
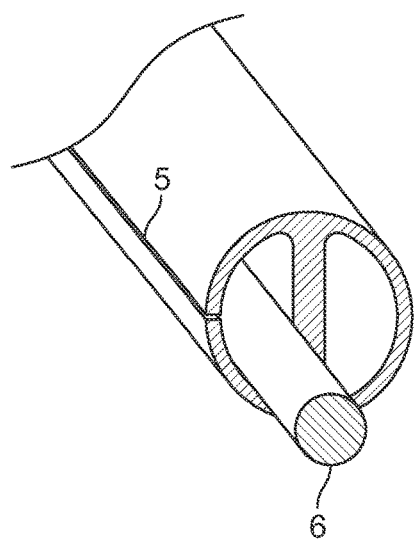
FIGS. 3A and 3B each illustrate schematized views of a novel catheter set according to the teachings of the present invention.

Likewise, FIG. 3A illustrates how guidewire (6) exists in a guidewire lumen, and is retained by the walls of the guidewire lumen. The slit (5 remains substantially closed to retain the guidewire (6).

Figure 3B:
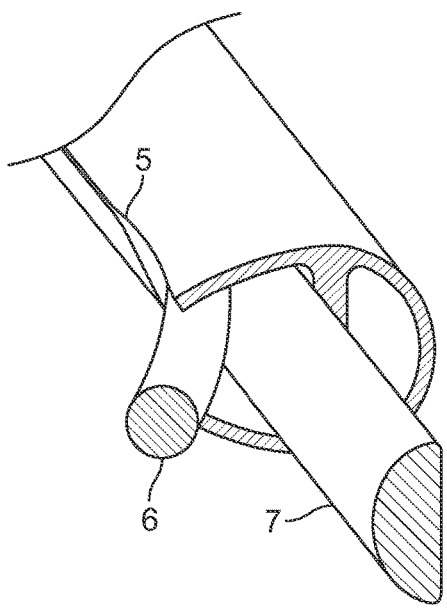

FIG. 3B illustrates ejector wire (7) being advanced, causing guidewire (6) to be pushed out of slit (5). Note that in this embodiment, the ejector wire and the guidewire lumen have similar and noncircular cross-sectional profiles. This ensures that the ejector wire (7) and guidewire (6) do not flip positions, resulting in the ejector wire passing out of the slit in the guidewire lumen.

FIG. 4 shows a cross-sectional view of the catheter, illustrating yet another important embodiment, where the guidewire is ejected due to the inflation of a bladder contained within the catheter. Turning now specifically to the other figures.

Figure 4A:
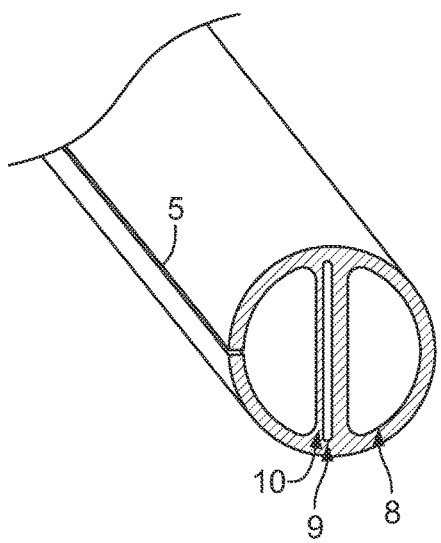
FIGS. 4A and 4B each illustrate schematized views of a novel catheter set according to the teachings of the present invention.

FIG. 4A illustrates the catheter shaft construction wherein therapeutic lumen (8) operates a balloon or other therapeutic element on the distal end of the catheter, wire ejection lumen (9) that is in fluid communication with a port on the proximal end of the catheter. A distensible wall (10) is shared between the wire ejection lumen (9) and the guidewire lumen (11). Those of skill in the art well understand how this embodiment is exchangeable for the prior discussed catheter system, thus further distinguishement has been omitted in the interest of clarity.

Figure 4B:
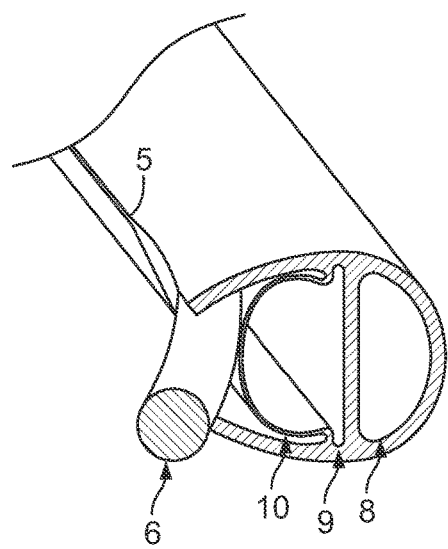

FIG. 4B shows that to eject a guidewire, a pressurized fluid is provided into the wire ejection lumen (9) causing the distensible wall (10) to expand outward into the guidewire lumen, which in turn pushes the guidewire (6) out through the slit (5).

While the method and apparatus have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference.

Finally, all references listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant.

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC § 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The many features and advantages of the invention are apparent from the detailed specification, and thus, it is intended by the appended claims to cover all such features and advantages of the invention which fall within the true spirit and scope of the invention. Further, because numerous modifications and variations will readily occur to those skilled in the art, it is not desired to limit the invention to the exact construction and operation illustrated and described, and accordingly, all suitable modifications and equivalents may be resorted to falling within the scope of the invention.

What is claimed is:

1. A catheter system, comprising:
   a catheter comprising a catheter body, a dividing wall extending along a diameter of the catheter body, and a distensible wall parallel to the dividing wall,
   the catheter defining a guidewire lumen between the distensible wall and an inner surface of the catheter body, a wire ejection lumen between the distensible wall and the dividing wall, and a therapeutic lumen opposite the guidewire lumen between the dividing wall and the inner surface of the catheter body, and
   the catheter body defining a slit at least partially along the guidewire lumen; and
   a guidewire configured to be inserted within the guidewire lumen of the catheter, wherein the distensible wall is configured to radially expand within the guidewire lumen when pressurized fluid is provided within the wire ejection lumen to push the guidewire out of the slit at least partially along the guidewire lumen without adjusting the lateral position of the guidewire in a body lumen.

2. The catheter system of claim 1, wherein the catheter further comprises a port at a proximal end of the catheter that is in fluid communication with the wire ejection lumen, the port being configured to receive the pressurized fluid.

3. The catheter system of claim 1, wherein the catheter further comprises a therapy device at a distal end of the catheter.

4. The catheter system of claim 3, wherein the therapy device is a balloon or a stent.

5. The catheter system of claim 3, wherein the therapeutic lumen is in fluid communication with the therapy device at the distal end of the catheter.

6. The catheter system of claim 1, wherein the therapeutic lumen is configured to deliver a therapeutic fluid.

7. The catheter system of claim 1, wherein the therapeutic lumen is an aspiration lumen.

8. The catheter system of claim 1, wherein the catheter further comprises at least two guidewire exit points, and wherein the slit is defined between the at least two guidewire exit points.

9. The catheter system of claim 1, wherein the guidewire lumen and the therapeutic lumen have similar non-circular cross-sectional profiles.

10. The catheter system of claim 9, wherein the guidewire lumen and the therapeutic lumen have D-shaped cross-sectional profiles.

11. The catheter system of claim 1, wherein the distensible wall is configured to unidirectionally expand into the guidewire lumen when pressurized fluid is provided within the wire ejection lumen.

12. A method for pushing a guidewire out of a guidewire lumen, the method comprising:
   receiving a catheter system, comprising:
      a catheter comprising a catheter body, a dividing wall extending along a diameter of the catheter body, and a distensible wall parallel to the dividing wall,
      the catheter defining a guidewire lumen between the distensible wall and an inner surface of the catheter body, a wire ejection lumen between the distensible wall and the dividing wall, and a therapeutic lumen opposite the guidewire lumen between the dividing wall and the inner surface of the catheter body,
      the catheter body defining a slit at least partially along the guidewire lumen,
      a guidewire configured to be inserted within the guidewire lumen of the catheter;
   causing-at least some of the guidewire to be received within the guidewire lumen of the catheter; and
   providing pressurized fluid within the wire ejection lumen to radially expand the distensible wall within the guidewire lumen to cause the guidewire to release through the slit at least partially along the guidewire lumen without adjusting a lateral position of the guidewire in a body lumen.

13. The method of claim 12, wherein providing the pressurized fluid within the wire ejection lumen comprises providing the pressurized fluid via a port at a proximal end of the catheter that is in fluid communication with the wire ejection lumen.

14. The method of claim 12, further comprising delivering a therapeutic fluid through the therapeutic lumen.

15. The method of claim 12, further comprising aspirating a fluid trough the therapeutic lumen.

16. The method of claim 12, wherein the guidewire lumen and the therapeutic lumen have similar non-circular cross-sectional profiles.

17. The method of claim 16, wherein the guidewire lumen and the therapeutic lumen have D-shaped cross-sectional profiles.

18. The method of claim 12, wherein providing the pressurized fluid within the wire ejection lumen to radially expand the distensible wall within the guidewire lumen to cause the guidewire to release through the slit at least partially along the guidewire lumen comprises providing pressurized fluid within the wire ejection lumen to unidirectionally expand the distensible wall within the guidewire lumen to cause the guidewire to release through the slit at least partially along the guidewire lumen.

* * * * *